(12) United States Patent
Iwankow (10) Patent No.: US 11,113,949 B1
(45) Date of Patent: Sep. 7, 2021

(54) HYGIENE APPARATUS AND METHOD

(71) Applicant: David Iwankow, Canoe Cove (CA)

(72) Inventor: David Iwankow, Canoe Cove (CA)

( * ) Notice: Subject to any disclaimer, the term of this patent is extended or adjusted under 35 U.S.C. 154(b) by 0 days.

(21) Appl. No.: 17/094,730

(22) Filed: Nov. 10, 2020

Related U.S. Application Data (60) Provisional application No. 63/080,484, filed on Sep. 18, 2020.

(51) Int. Cl.
| | |
|---|---|
| *G08B 23/00* | (2006.01) |
| *G08B 21/24* | (2006.01) |
| *G07C 1/10* | (2006.01) |
| *A61L 2/24* | (2006.01) |
| *H02J 50/00* | (2016.01) |
| *H02J 50/10* | (2016.01) |

(52) U.S. Cl.
CPC .............. *G08B 21/245* (2013.01); *A61L 2/24* (2013.01); *G07C 1/10* (2013.01); *H02J 50/005* (2020.01); *H02J 50/10* (2016.02)

(58) Field of Classification Search
CPC ...... G08B 21/245; H02J 50/10; H02J 50/005; A61L 2/24; G07G 1/10
USPC ...................................................... 340/573.1
See application file for complete search history.

(56) References Cited

U.S. PATENT DOCUMENTS

| | | | |
|---|---|---|---|
| 4,896,144 A | 1/1990 | Bogstad | |
| 6,236,317 B1 * | 5/2001 | Cohen ................... | G08B 21/245 137/552.7 |
| 7,978,083 B2 | 7/2011 | Melker et al. | |
| 8,237,558 B2 * | 8/2012 | Seyed Momen ..... | G01S 1/7034 340/539.11 |
| 2002/0019709 A1 * | 2/2002 | Segal ....................... | G07C 3/10 702/45 |
| 2002/0061500 A1 * | 5/2002 | Collopy .............. | G09B 19/0076 434/238 |
| 2009/0195385 A1 * | 8/2009 | Huang .................... | G16H 40/20 340/572.1 |
| 2009/0267776 A1 * | 10/2009 | Glenn ................... | G08B 21/245 340/573.1 |
| 2011/0068930 A1 * | 3/2011 | Wildman ................ | G16H 40/20 340/573.1 |
| 2011/0169645 A1 * | 7/2011 | Cartner ................... | G16H 40/20 340/573.1 |

(Continued)

FOREIGN PATENT DOCUMENTS

| | | |
|---|---|---|
| WO | WO 2010028320 A1 | 3/2010 |

*Primary Examiner* — Kerri L Mcnally
*Assistant Examiner* — Thang D Tran
(74) *Attorney, Agent, or Firm* — David W. Carstens; J. Miguel Hernandez; Carstens & Cahoon, LLP (57) ABSTRACT

A system for monitoring and maintaining hand washing compliance. The system may be configured to monitor hand washing compliance at any hand washing station having a water faucet and cleaning agent. The system may comprise a wristband, a wash node, a control unit, and a database. The wash node may be configured to capture the activity within an area encompassing the hygiene station. The system is configured to monitor and notify the user of when to clean their hands. Further, the system can provide real time and historical monitoring of hygiene compliance and policy violation by users. Further, the system can provide the user with notifications of their compliance through visual or wireless device notifications indications of the time elapsed since a previous washing.

20 Claims, 11 Drawing Sheets

(56) References Cited

U.S. PATENT DOCUMENTS

| | | | |
|---|---|---|---|
| 2011/0193703 A1* | 8/2011 | Payton | G08B 21/245 340/573.1 |
| 2011/0227740 A1* | 9/2011 | Wohltjen | G01S 11/16 340/573.1 |
| 2011/0254682 A1* | 10/2011 | Sigrist Christensen | G08B 21/245 340/539.12 |
| 2012/0062382 A1* | 3/2012 | Taneff | G08B 21/245 340/573.1 |
| 2012/0112906 A1* | 5/2012 | Borke | G08B 21/245 340/539.13 |
| 2013/0027199 A1* | 1/2013 | Bonner | G08B 21/245 340/539.11 |
| 2013/0113619 A1* | 5/2013 | Snodgrass | G07C 11/00 340/539.11 |
| 2014/0104062 A1* | 4/2014 | Weiner | G08B 21/245 340/573.1 |
| 2014/0180713 A1* | 6/2014 | Tenarvitz | G16H 40/20 705/2 |
| 2014/0279603 A1* | 9/2014 | Ortiz | G08B 21/245 705/317 |
| 2015/0022361 A1* | 1/2015 | Gaisser | H01L 27/14627 340/573.1 |
| 2015/0134357 A1* | 5/2015 | Davis | A61B 90/80 705/2 |
| 2015/0161874 A1* | 6/2015 | Thyroff | G08B 25/10 340/539.11 |
| 2015/0254965 A1* | 9/2015 | Moore | G08B 21/245 340/539.12 |
| 2016/0042635 A1* | 2/2016 | Rosebraugh | G16H 40/20 340/573.1 |
| 2016/0267772 A1* | 9/2016 | Iseri | G16H 40/20 |
| 2016/0275778 A1* | 9/2016 | Wallace | G08B 21/245 |
| 2017/0076581 A1* | 3/2017 | Felch | G06F 3/017 |
| 2017/0256155 A1* | 9/2017 | Sengstaken, Jr. | G06K 7/10009 |
| 2018/0014778 A1* | 1/2018 | Cronin | G16H 40/67 |
| 2018/0047277 A1* | 2/2018 | Thyroff | G08B 21/24 |
| 2018/0293873 A1* | 10/2018 | Liu | G06K 7/10366 |
| 2018/0357886 A1* | 12/2018 | Tavori | G06F 1/163 |
| 2019/0228640 A1* | 7/2019 | Freedman | G16H 40/20 |
| 2019/0354753 A1* | 11/2019 | Worrall | G06K 9/00087 |
| 2020/0202319 A1* | 6/2020 | Forutanpour | G07F 7/06 |
| 2020/0302775 A1* | 9/2020 | Liu | G08B 21/245 |

* cited by examiner

```
┌─────────────────────────────┐
│  INITIATE BAND INTERACTION  │── 702A
│       WITH WASH NODE        │
└─────────────────────────────┘
              │
              ▼
┌─────────────────────────────┐
│   BAND DISPLAYS WASHING     │── 704A
│         INDICATION          │
└─────────────────────────────┘
              │
              ▼
┌─────────────────────────────┐
│   INITIATE WASH FOR FIRST   │── 706A
│        PERIOD OF TIME       │
└─────────────────────────────┘
              │
              ▼
┌─────────────────────────────┐
│   BAND DISPLAYS WASHED      │── 708A
│         INDICATION          │
└─────────────────────────────┘
              │
              ▼
┌─────────────────────────────┐
│  COMMENCE BAND INTERACTION  │── 710A
│       WITH WASH NODE        │
└─────────────────────────────┘
              │
              ▼
┌─────────────────────────────┐
│  BAND DISPLAYS COMPLIANT    │── 712A
│         INDICATION          │
└─────────────────────────────┘
              │
              ▼
┌─────────────────────────────┐
│       INITIATE TIMER        │── 714A
└─────────────────────────────┘
```

HYGIENE APPARATUS AND METHOD

CROSS-REFERENCE TO RELATED APPLICATIONS

This application claims the benefit of U.S. Provisional Application No. 63/080,484, filed Sep. 18, 2020 entitled "Hygiene Apparatus and Method," the disclosure of which is incorporated herein by reference.

TECHNICAL FIELD

The present disclosure relates to a hygiene apparatus and methods of increasing the hygiene of a user by providing visual indicators and reminders to the user.

BACKGROUND

Hand washing and glove changing are critical to the prevent the spread of germs, pathogens, and disease. Insufficient hand cleanliness in areas of high contact increases the chances of a spread of germs, pathogens, and disease. Currently, some local, state, and federal regulators have implemented requirements on all employees to wash their hands at specific times of their workday. And, some food-service or other operators have instituted policies requiring hand washing or glove changes at specified intervals. However, the effectiveness of such handwashing and enforcement of such requirements are less than uniform. Generally, employers rely on rudimentary techniques such as warning signs and periodic announcements to remind employees to wash their hands. Some newer techniques rely on location-based devices to notify an employee to wash their hands. There currently are no techniques to assess compliance of an employee washing their hands. Further, there currently are no techniques to provide clear, visual updates to the employee, employers, managers and surrounding people of the compliance of the employee's hand washing.

A further need exists to overcome the problem of insufficient hand washing reminders and monitoring system for policy compliance. There is a further need to overcome the problem of assessing the cleanliness of an employee's washed hands. There is a further need to provide the status of an employee's hand cleanliness to the surrounding people.

SUMMARY

The present disclosure relates to a system and method for monitoring and maintaining hand washing compliance with a wash protocol. The system may be configured to monitor hand washing compliance at any hand washing station having a water faucet and cleaning agent. The system may comprise a portable electronic device and a wash node. The wash node may be configured to capture wash data, associate wash data with a unique identifier, transmit wash data and a unique identifier to the control unit for wash determination of compliance, and transmit determination results to the portable electronic device. The system may be configured to monitor and notify the user of when to clean their hands. Further, the system can provide real time monitoring of hygiene compliance and policy violation by users. Further, the system can provide the user with notifications of their compliance through visual indications of the time elapsed since a previous washing.

The system may be configured to monitor and maintain glove change compliance with a glove protocol. The system may comprise a portable electronic device and a wash node. The wash node may be configured to capture wash data, present time of wash duration or other animated information, associate wash data with a unique identifier, transmit wash data and a unique identifier to the control unit for wash determination of compliance, and transmit determination results to the portable electronic device. The system may be configured to monitor and notify the user of when to change their gloves. Further, the system can provide real time monitoring of glove compliance and policy violation by users. Further, the system can provide the user with notifications of their compliance through visual indications of the time elapsed since a previous washing.

The system may be configured to monitor and maintain hand sanitizing compliance with a hand sanitizing protocol. The system may comprise a portable electronic device and awash node. The wash node may be configured to capture wash data, associate wash data with a unique identifier, transmit wash data and a unique identifier to the control unit for wash determination of compliance, and transmit determination results to the portable electronic device. The system may be configured to monitor and notify the user of when to sanitize their hands. Further, the system can provide real time monitoring of hand sanitizing compliance and policy violation by users. Further, the system can provide the user with notifications of their compliance through visual indications of the time elapsed since a previous washing.

BRIEF DESCRIPTION OF THE DRAWINGS

For a fuller understanding of the advantages provided by the current disclosure, reference should be made to the following detailed description together with the accompanying drawings wherein.

FIC. 9 is an illustration of an embodiment of a wristband; and

DETAILED DESCRIPTION

Figure 1:
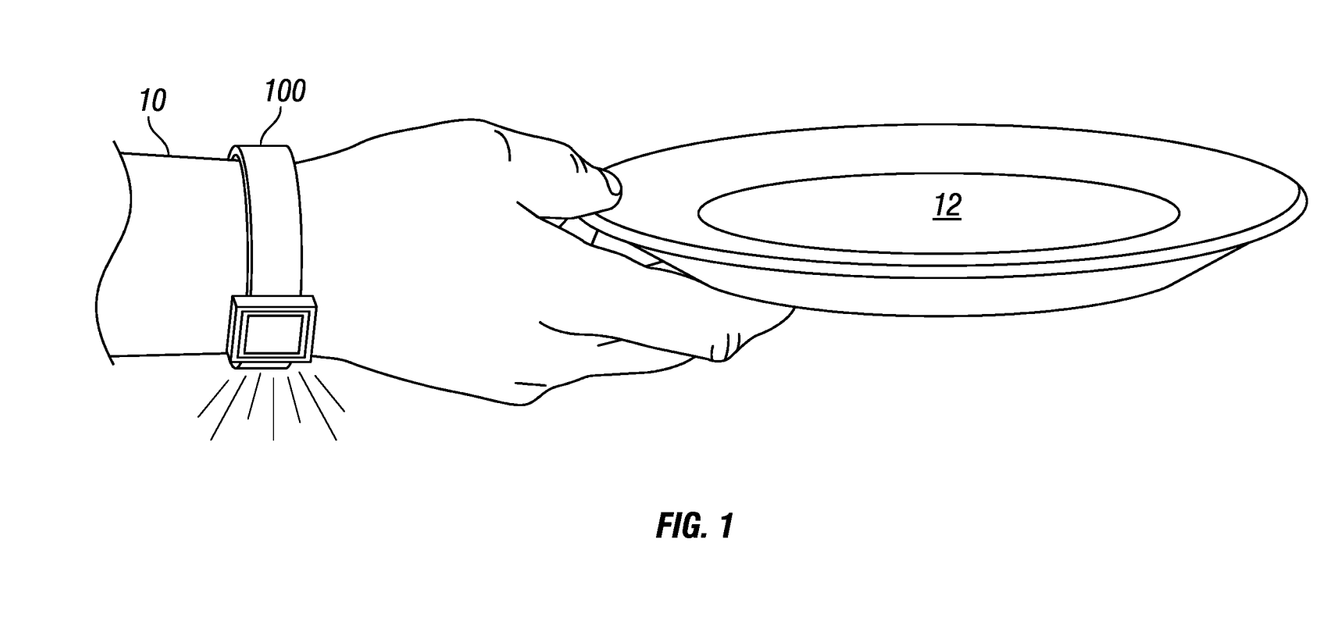
FIG. 1 is an illustration of an embodiment of a hygiene monitoring system.
Figure 9:
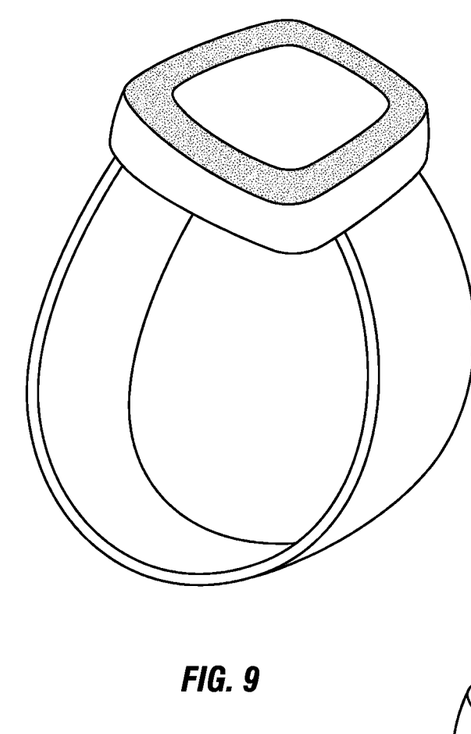
Figure 10:
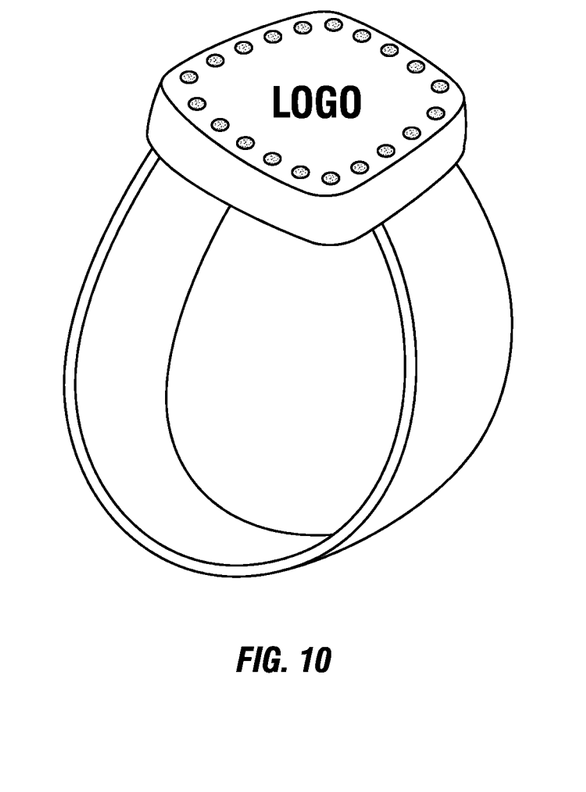
FIG. 10 is an illustration of an embodiment of a wristband.

FIG. 1 illustrates an embodiment of a wristband 100 (alternatively referred to as a portable electronic device) for monitoring and maintaining hygiene compliance. In settings such as hospitality and essential and front line workers, it may be important that employees are complying with the health and safety protocols of the establishment. One example of a health and safety protocol may be hand washing compliance, where employees must periodically clean their hands while working a shift. Additionally, the system for monitoring and maintaining compliance with hygiene protocols may be applied to individuals of various locations, such as customers in establishments, which enables the establishment to monitor the compliance of both employees and customers hygiene maintenance and ensure a compliant environment. The user 10, which in one example may be a food server, wears the wristband 100 while working during a shift. Additionally, other non-limiting configurations of wristbands are illustrated in FIG. 9 and FIG. 10. As an example, the employee (alternatively referred to herein as a user) 10 may be serving a plate of food 12 and the wristband may be configured to display a variety of indications. The indications may be flashing or static lights in various colors, which enable the user's supervisors, fellow employees, and surrounding people, such as consumers or customers, to know whether the user is complying with the hand washing protocols of the establishment. Alternatively, a wristband may be configured to be secured to the outer clothing of the user, such as in the form of a badge clasped to the user's pants or shirt, or neck hanging lanyard. The wristband may be secured to the user in a location where the display is visible to the camera and surrounding people. These configurations of the wristband encourage safe practices among users because the visible location of the wristband makes surrounding people aware that the user is complying with proper hand washing techniques, glove change, and/or hand sanitizing policies. In some embodiments, a wristband might be configured to create a visual or audible signal on an application on the supervisor' or patron's phone.

Figure 2:
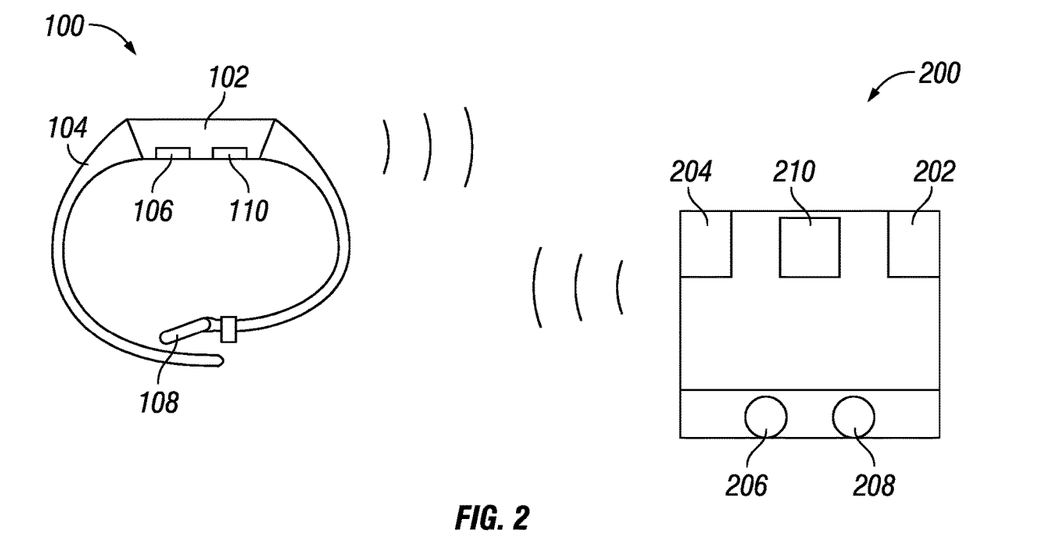
FIG. 2 is an illustration of an embodiment of a wrist band and a wash node in communication.

With reference to FIG. 2, an illustration of a wristband 100 communicatively coupled to a wash node 200 is depicted. The wristband 100 may include a band 104, a clasp 108, a body having an electronic pack 102, a sensor 106, and a wireless communication unit 110. In some examples, the sensor 106 may be a heat or temperature sensor, which could be configured to detect whether the user has a fever. Additionally, the sensor 106 may be configured to track the motion of the user, such as the number of steps the user has taken or the positional location of the user. This activity may be analyzed to determine the user's activity during a given shift. Additionally, the sensor 106 may be a gyroscope that may be configured to record the user's movement, such as the motion and intensity of the user's hands. This information may analyzed to determine whether the user washed their hands with sufficient vigor. The electronic pack 102, which may be removably coupled to a pocket in the wristband 100, may include a processor and a rechargeable battery. The wash node 200 may include a processor 202, a communications device 204, a set of sensors configured to capture wash data, and a display 210 (e.g., LEDs or led panel). The set of sensor may include at least one image capture device 206, and at least one near-field communication device 208. The display 210, may be configured to present animation data (e.g., flash a pattern when the wristband 100 is scanned to the wash node 200). The animation data being presented may signify that the sequence is commencing, pending, or concluding. The display 210 may also be configured to present, in seconds for example, the duration of the sequence or other information. It is understood that a set of sensors means one or more sensors. Examples of an image capture device 206 may include a photographic camera, an infrared sensor (IR) or a video camera. Examples of a near-field communication device 208 may include an RFID scanner. In some embodiments, the image capture device 206 may be configured to detect whether a user has a fever (e.g., body temperature above a threshold amount). In one example, the wash node 200 detects the presence of the wristband 100 within a distance of about 1 cm to 5 cm. Additionally, the wash node 200 may be configured to obtain wash data collected by the portable electronic device. Wash data includes information collected by the sensor 106 in the wristband 100.

Figure 3:
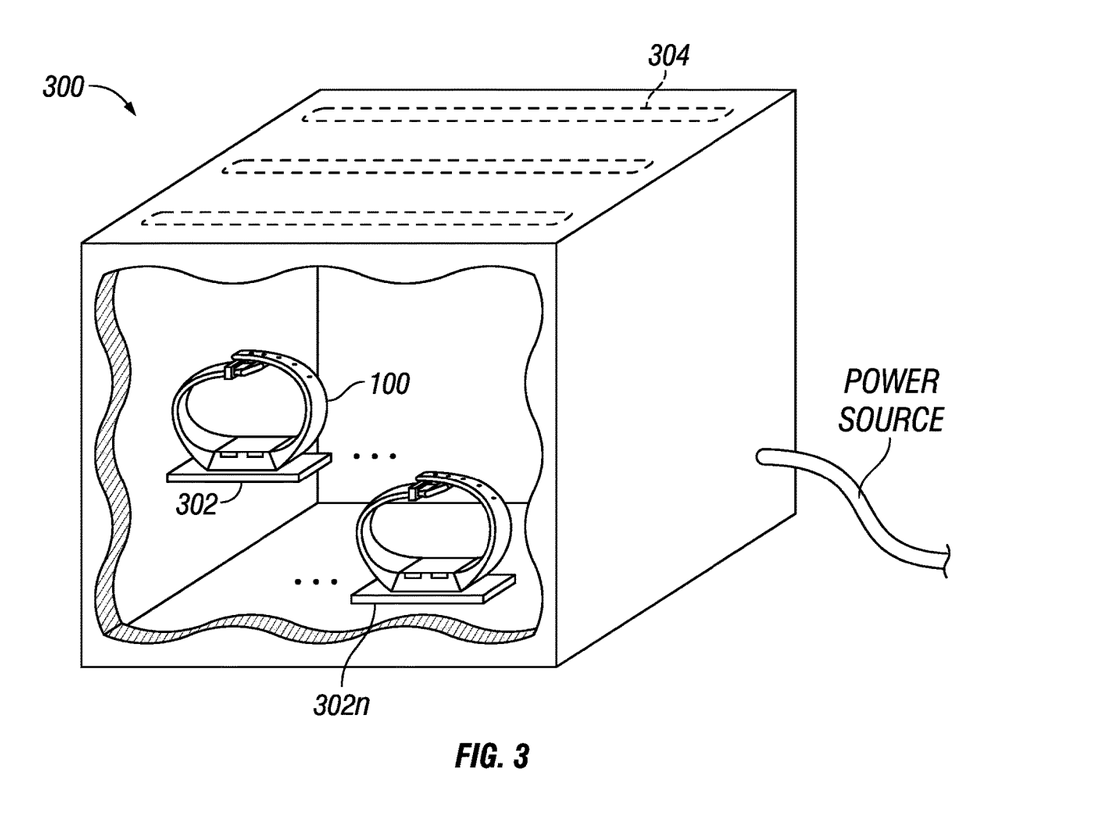
FIG. 3 is a perspective view of an embodiment of a charging station and sanitizer.

Because the wristband 100 may be worn by various users at different times, each wristband will need to be sanitized after a user has completed a work shift. Additionally, the rechargeable battery will have become depleted after a given period of time will need to be recharged before the next user begins using it for their next work shift. Referring to FIG. 3, a charging and sanitizing station 300 may be configured to disinfect each wristband 100 and recharge the batteries. The charging and sanitizing station 300 may include UV lights 304 that are configured to destroy bacteria, viruses, fungi, and spores. Additionally, the charging and sanitizing station 300 may utilize other sanitizing methods such as ozone disinfection as taught by Gil et al. (US2016/0101202) and Campagna (US 2015/0231288). The charging and sanitizing station 300 may also include a charging dock 302 for each wristband 100. The charging dock 302 may be a wired connection or a wireless connection (such as the inductive charging taught in U.S. Pat. No. 8,629,651) to recharge the batteries. In one embodiment, the charging dock 302 may utilize Qi Coils™. The charging and sanitizing station 300 further includes a power source 306.

Figure 4:
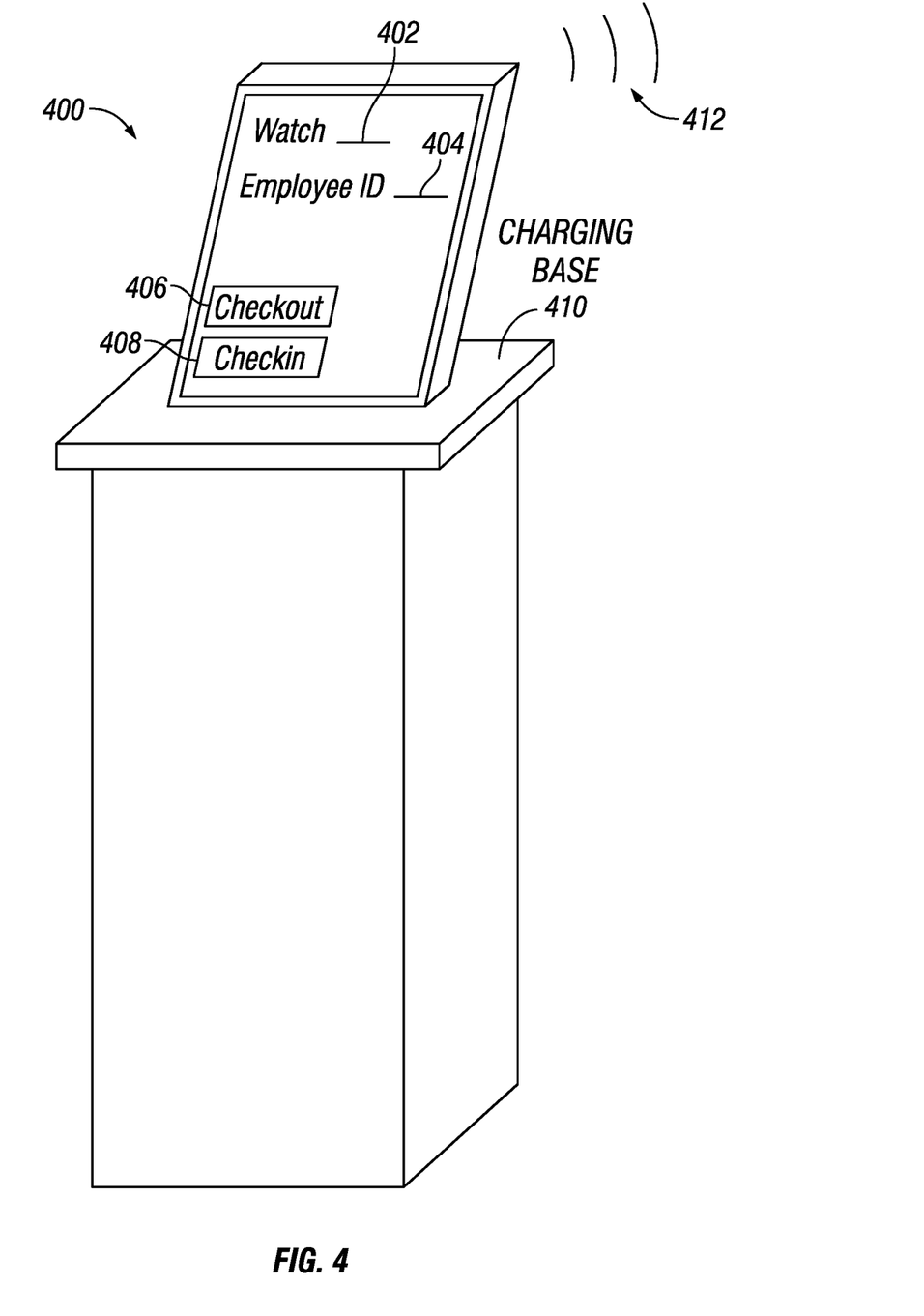
FIG. 4 is a perspective view of an embodiment of a checkout kiosk.

With reference to FIG. 4, a user must checkout and check-in the wristband band from a kiosk 400. The kiosk 400, which may be connected to a charging base 410, may be configured to tether the user ID 404 to a specific wristband 402. In some examples, the user specifies whether they are checking-out 406 or checking-in 408 the wrist band. The kiosk may be configured to be in communication 412 with the other elements of the system, which allows for an up-to-date status of which user has which wristband. As will be further explained, the kiosk enables the database to create compliance dashboards associated with the employee and unique identifier (e.g., serial number on the wristband) that enable a hygiene manager to monitor the hand washing compliance. In one example, the kiosk 400 may be configured to be part of the charging and sanitizing station.

Figure 5:
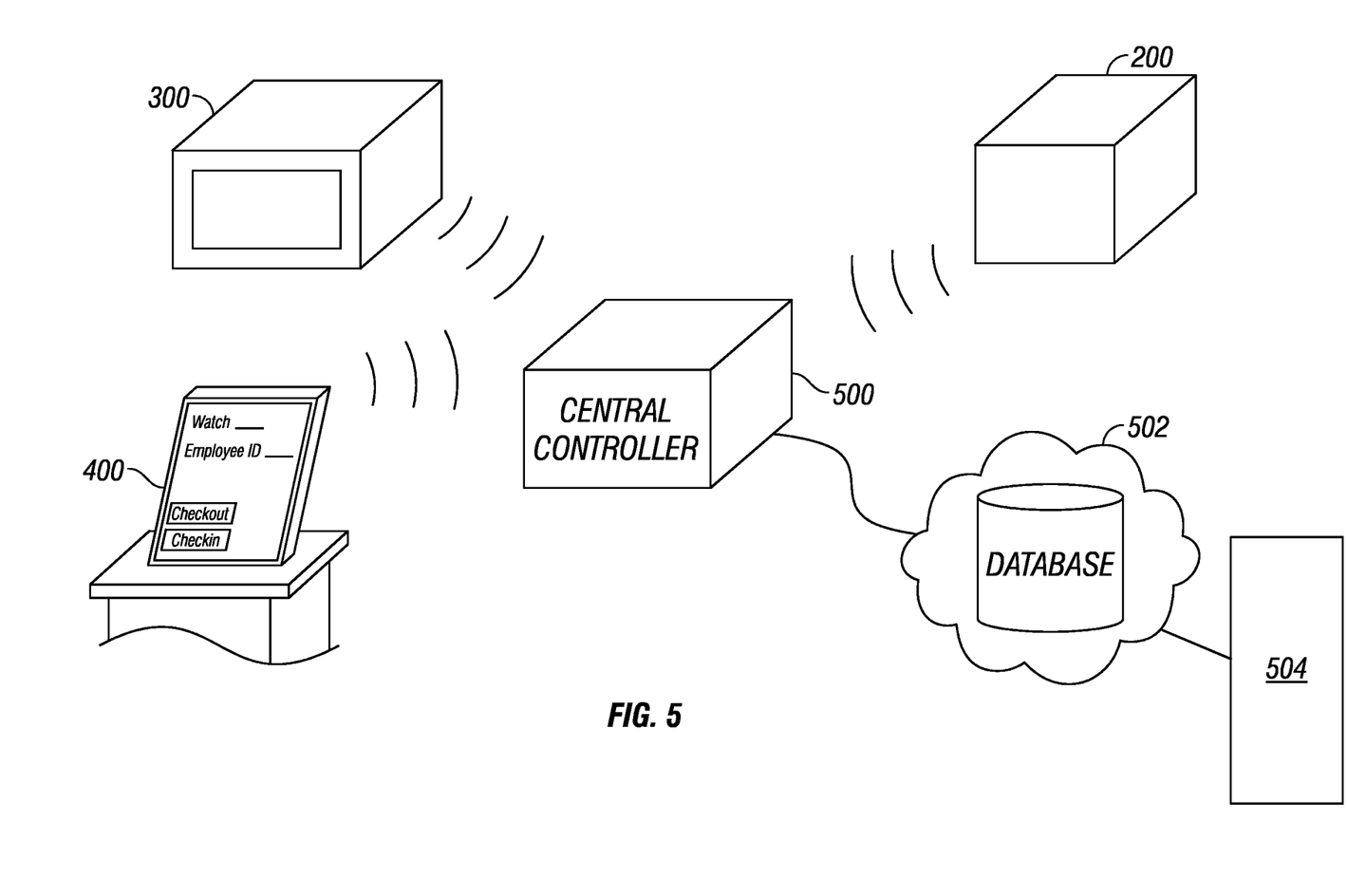
FIG. 5 is a diagram illustrating an embodiment of a hygiene monitoring system.

Referring to FIG. 5, a diagram of one embodiment of the hygiene monitoring system is depicted. A central controller 500 (alternatively referred to as a control unit) may be configured to be in communication with the wash node 200, charging and sanitizing station 300, and the kiosk 400. The central controller 500 generates and/or collects wash data sets from the other units (200, 300, and 400) for processing. In at least one embodiment, the central controller 500 generates and/or collects wash data sets from the other units (200, 300, and 400) for processing and/or storage in a database 502. The database 502 may be physically installed in the central controller 500 or in communication with the central controller 500 via cloud communication. A dashboard (or front-end user system) 504 may be connected or in communication with the database 502 to review processed data. In some embodiments, the dashboard 504 may be communicatively coupled to the central controller 500. The central controller 500 may be configured to provide real-time updates of the status of each wristband and the data collected by each wristband. In some examples, the wash data may be analyzed and presented in a viewable compliance dashboard for review by the hygiene manager. One example of a viewable compliance dashboard is the live-band status dashboard, which presents a running total of compliance status logged for each user's band at any given time of day. Another example is the active shift dashboard, which presents the current status of each user's band, each user's shift compliance rating, and overall compliance rating. The compliance ratings enable the hygiene manager to focus on users that are struggling to maintain hand washing compliance and ensure that they focus on improving. Thus, systems such as this ensure that customers and fellow employees are not put at an additional health risk. Another example is the current default alert dashboard, which tabulates the number of default alerts each user has logged for the current shift. Another example is the total default dashboard, which tabulates the total number of default alerts for all users for a given time period (e.g., daily, weekly, bi-weekly, monthly, etc.). In one embodiment, the database may be configured to collect and categorize information from users across multiple connected locations of an operation or region and enables consolidated statistics and metrics. Another example may be viewing the wristbands that are in an "off" configuration.

Figure 8:
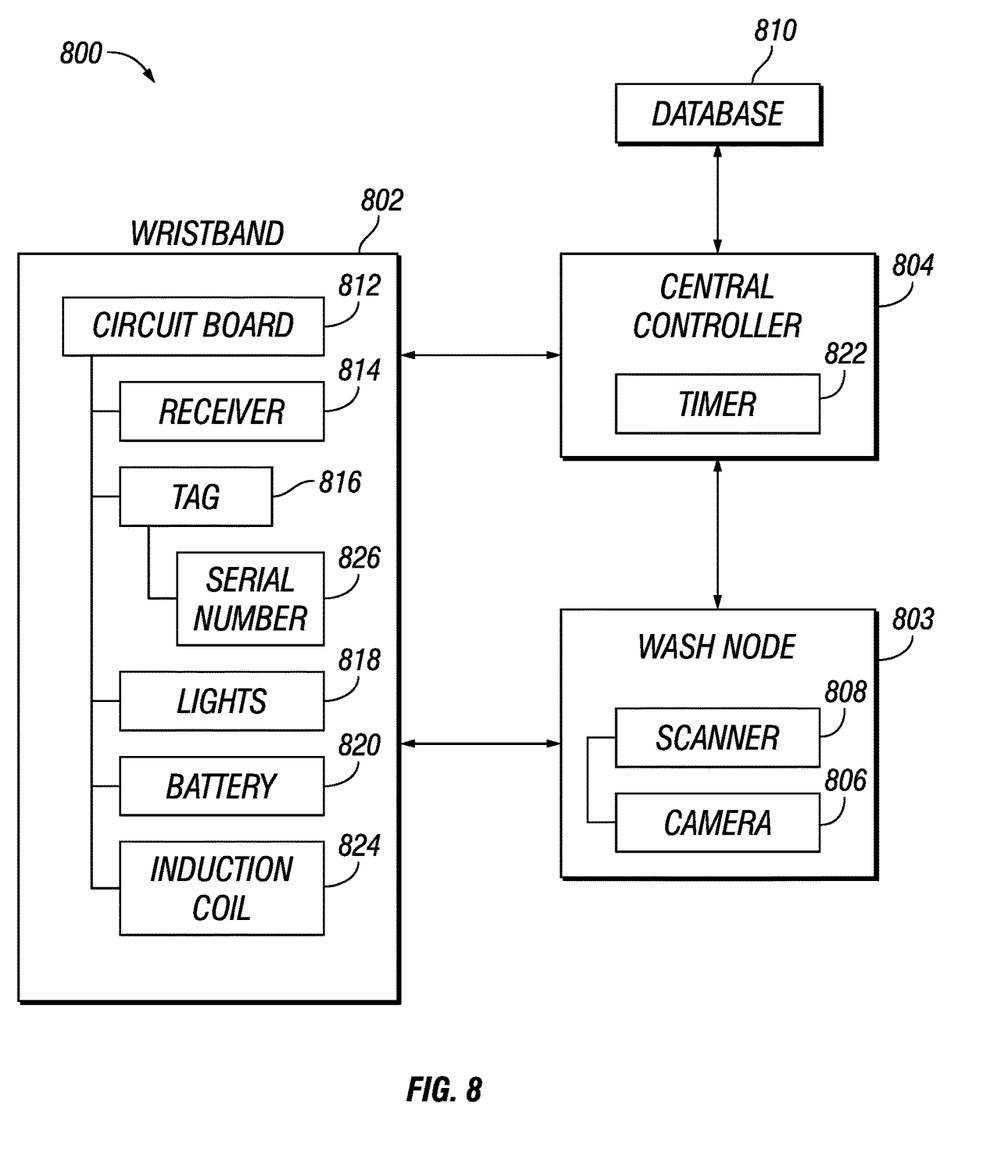
FIG. 8 is a block diagram of an embodiment of a hygiene monitoring system.

Referring to FIG. 8, a block diagram illustrating one embodiment of the hygiene monitoring system 800 is depicted. The system 800 may comprise a wristband 802, a central controller 804, a wash node 803, and a database 810. The central controller may include a timer 822, memory, and a processor. It is understood that a skilled artisan would recognize that memory and a processor are inherent features of such a controller. The wristband 802 may include a printed circuit board 812 having a receiver 814, a tag 816, at least one light 818, and a battery 820. In an alternate configuration, the wristband further comprises an induction coil 824. In one example, the tag 816 may be a radio frequency identification (RFID) tag and has a corresponding unique identifier or serial number 826. The receiver 814 may be a wireless protocol receiver that may be configured to receive data. The one or more lights 818 may be light emitting diodes (LEDs) that are configured to emit a variety of colors. The induction coil 824 may be configured to enable wireless charging of the battery 820. Alternatively, the battery 820 may be configured to be charged via a direct pin charging. In another embodiment, the tag 816, the one or more lights 818, and the battery 820 are housed in a removable electronic pack (not shown). The removable pack enables the wristband to be sanitized separately from the electronic pack. The wash node 803 may include a scanner 808 and a camera 806. In some examples, the scanner 808 may be an RID scanner that may be configured to detect the tag 816. The camera 806 may be a video or still camera configured to capture images of the hand washing sink and surrounding areas. Additionally, the camera 806 may be an infrared camera that may be configured to capture the temperature of a user. In one example, the camera may be configured to capture images for every second at the basin of the hygiene station. When the user is out of hand washing compliance, the lights 818 on the wristband 802 are configured to display a default indication that notifies the user to wash their hands immediately. An example of a default indication may be a red flashing light.

With continued reference to FIG. 8, in one embodiment, the central controller 804 is configured to be in communication with the wristband 802, the wash node 803, and the database 810. In another embodiment, the central controller 804 is configured to be in communication with the wristband 802, and the wristband 802 is configured to be in communication with the wash node 803. In another embodiment, the central controller 804 is configured to be in communication with the wash node 803, and the wash node 803 is configured to be in communication with the wristband 802. Additionally, the wash node 803 may be configured to include the central controller 804 instead of the central controller 804 being located remotely.

Figure 7A:
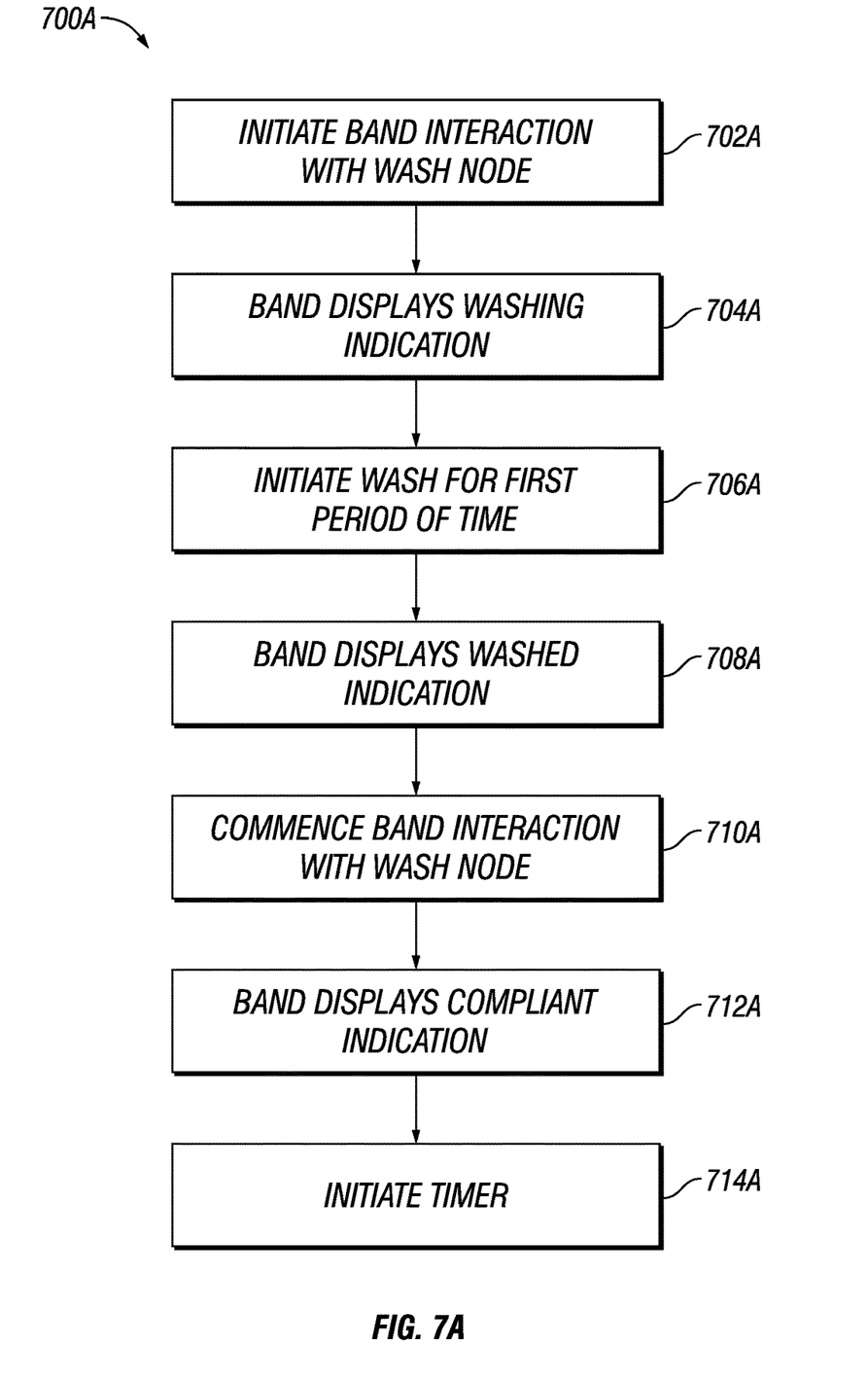
FIG. 7A is a flowchart illustrating an embodiment of a wash sequence.

Referring to FIG. 7A, a flowchart 700A of an embodiment of a hand washing sequence is illustrated. To begin the wash sequence, the user scans 702A the wristband with the scanner, wherein the scanner detects the tag and transmits the serial number to the controller central controller. Once the serial number is registered in the database, the central controller runs a timer for a first period of time 706A and activates the camera. In some embodiments, the wash node is configured to present the running time on a display. Once the timer begins running for the first period of time, the central controller sends a washing signal 704A to the wristband, which generates an alert to notify the wristband that the wash protocol has been initiated. An example of an alert is a prompt for the lights to display a washing indication. The timer is configured to correlate elapsed time with the captured wash data. An example of a washing indication may be a blue flashing light.

After the timer runs for a configurable or predetermined time period of, for example from about 20 to about 30 seconds, the central controller sends a washed signal to the wristband, which generates an alert to notify the wristband that the wash protocol has expired. An example of an alert is a prompt for the lights to display a washed indication 708A. An example of a washed indication may be a solid blue light. Upon completion of washing their hands, the user scans the wristband a second time 710A with the wash node, wherein the wash node sends the serial number to the central controller. Once the central controller receives the serial number, the central controller stops the timer and the camera and records the end time. The central controller sends the end time and captured images to the database, which may be stored in a dataset corresponding to the serial number. After sending the information to the database, the controller sends a clean signal to the wristband, which generates an alert to notify the wristband that the wash protocol has been satisfied. An example of an alert is a prompt for the lights to display a clean indication 712A. An example of a clean indication may be a solid green light. In an alternate embodiment, if the user attempts to scan the wristband before the first period of time has elapsed, the central controller will send a second washing signal to the wristband that will require the user to repeat hand washing. After sending the clean signal, the central controller runs the timer 714A for a second period of time, which may be from about 1 minute to about 30 minutes.

Figure 7B:
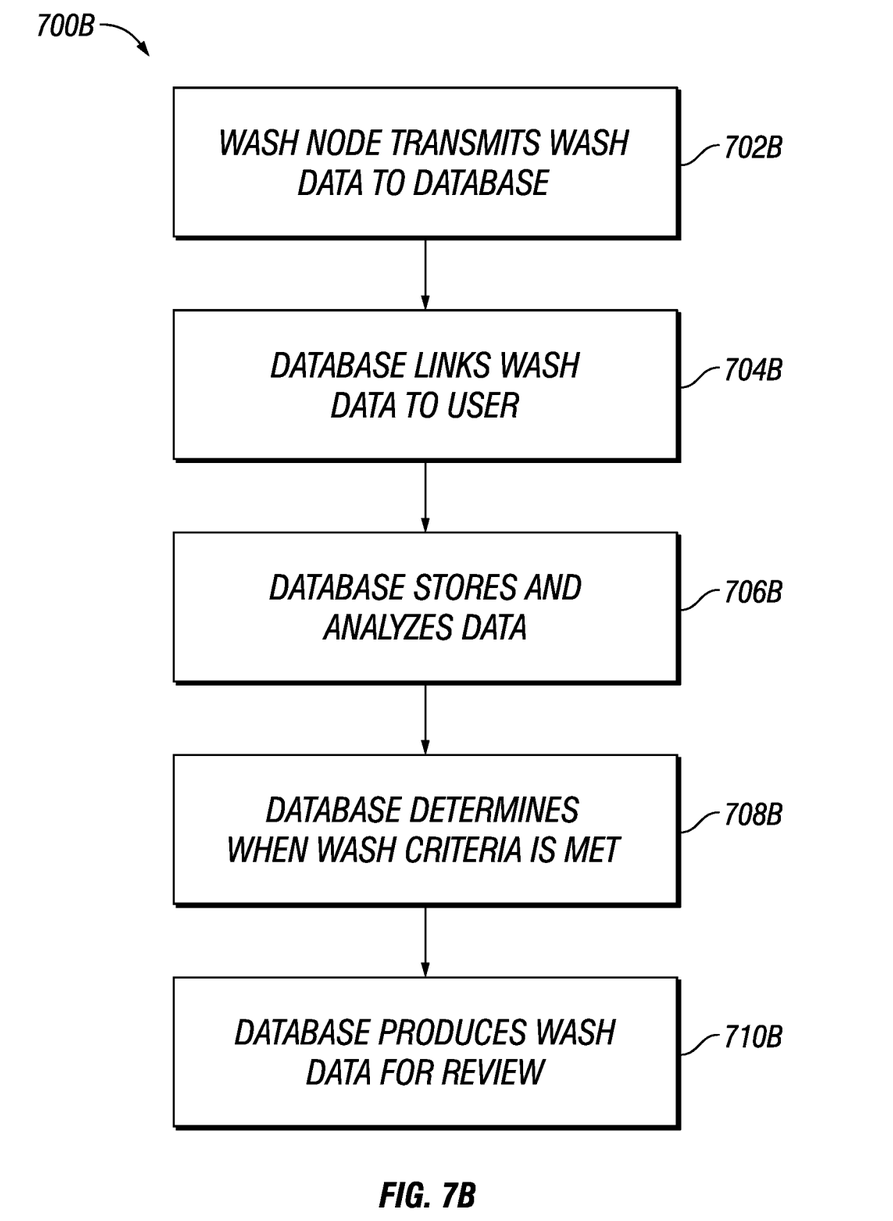
FIG. 7B is a flowchart illustrating an embodiment of a coordination of wash data.
Figure 7C:
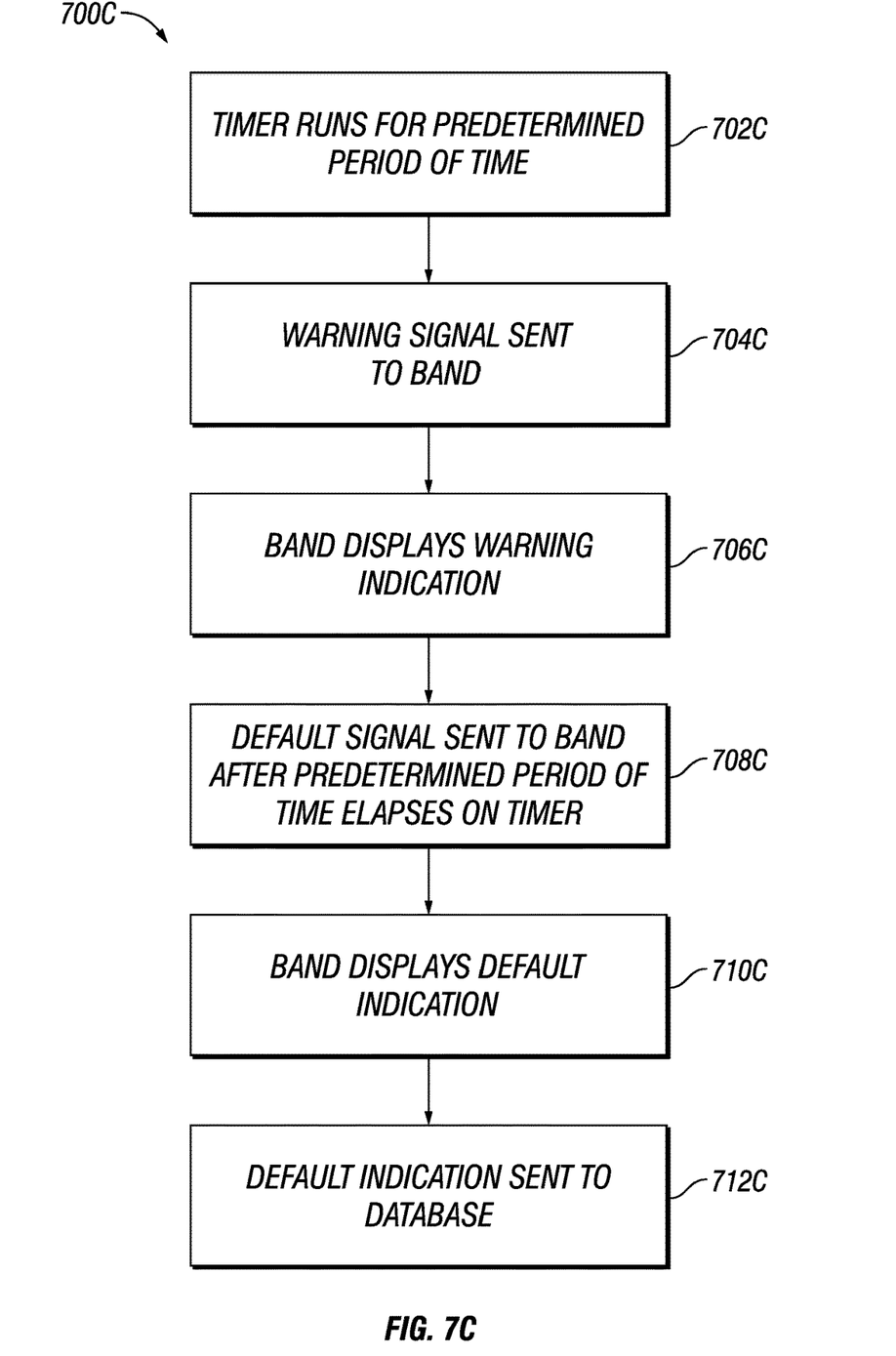
FIG. 7C is a flowchart illustrating an embodiment of a reminder to re-wash hands.

Referring to FIG. 7C, a flowchart 700C of an embodiment of a hand wash sequence is illustrated. After the timer runs for the second period of time 702C, the central controller sends a warning signal 704C to the wristband, which generates an alert to notify the wristband that the wash protocol is about to expire. An example of an alert is a prompt for the lights to display a warning indication 706C. An example of a warning indication may be a solid yellow light. Next, the timer starts to run for a third period of time, which may be from about 1 minute to about 30 minutes. After the third period of time has elapsed, the central controller sends a default signal 708C to the wristband, which generates an alert to notify the wristband that the wash protocol has expired. An example of an alert is a prompt for the lights to display a default indication 710C. An example of a default indication may be a flashing red light. Additionally, a default indication may be recorded in the database 712C for review by the hygiene manager. Additionally, the central controller and/or the database may be configured to automatically detect the end of a shift, or a user forgetting to charge and/or return a wristband, and automatically signs the user out. Additionally, the system may be configured to enable the bands to trouble shoot themselves by, for example, communicating fault conditions to the database for action and notifications.

With reference to FIG. 7B, a flowchart 700B of an embodiment of a hand wash sequence is illustrated. The wash node may further be configured to send a copy of all captured information to the database 702B. Once the captured information is transmitted to the database, the serial number associated with the wristband enables the information to be linked with the correct user 704B. The sever may be configured to detect 706B whether the user's hands were present in the captured images and if their hands were moving. In another alternate embodiment, the server analyzes the information and cross-references it with effective hand washing techniques to determine the quality of the captured hand washings. For example, the database may be configured to identify the various types of hand motion the user utilized and for how long the user washed their hands. In these examples, if the server determines that the user did not utilize sufficient handwashing, the user will be required to repeat the handwashing process. Additionally, the system may further comprise a second camera configured to detect an inert agent that is added to the cleaning agent. For example, when the second camera detects the presence of the inert agent, the database will confirm that the user is washing their hands with approved cleaning agents. As the database receives the captured information, it may be configured to determine when the wash criteria is met (i.e., when the user is in compliance with the hand washing policy). The database may be configured to process the captured information and display the information in compliance dashboards for review by the hygiene manager 710B.

Figure 7D:
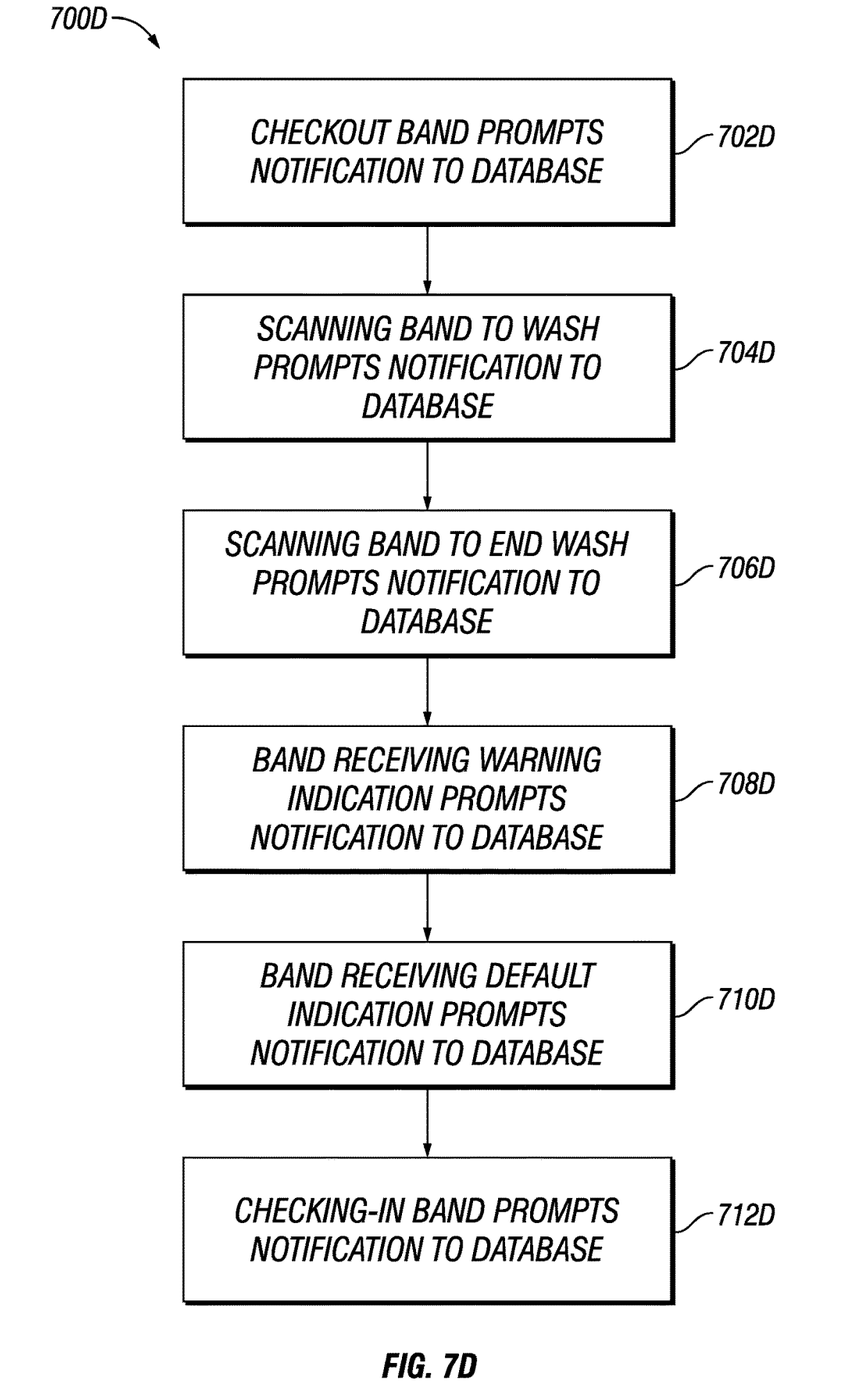
FIG. 7D is a flowchart illustrating an embodiment of alerting a hygiene manager.

Referring to FIG. 7D, a flowchart 700D depicting an embodiment of alerting a hygiene manager of wash data. The charging and sanitizing station transmits a notification 702D to the central controller when the user checks out a wristband from the charging and sanitizing station, which enables the hygiene manager to review which users must be in compliance with the handwashing policy. Following initiation of the washing sequence, the wash node transmits a notification 704D to the central controller that the user has started the handwashing sequence. Following successful completion of the handwashing sequence and scanning the wristband with the wash node, the wash node transmits a notification 706D to the central controller that the user is in compliance with the hand washing protocol. Once the warning indication is transmitted to the wristband, a notification 708D may be documented in the database for review by the hygiene manager. For instances where the user receives a default indication for being out of compliance with the hand washing policy, a notification 710D may be documented in the database for review by the hygiene manager. The out-of-compliance notification 710D enables the hygiene manager to direct the user to hand washing station and prevent the user from coming into any unauthorized contact with customers. When the user has completed their scheduled shift and checks-in their wristband with the charging and sanitizing station, the charging and sanitizing station transmits a notification 712D to the central controller that the wristband is no longer in use. This notification 712D may be updated in the database and cease data collection for that wristband.

Figure 6:
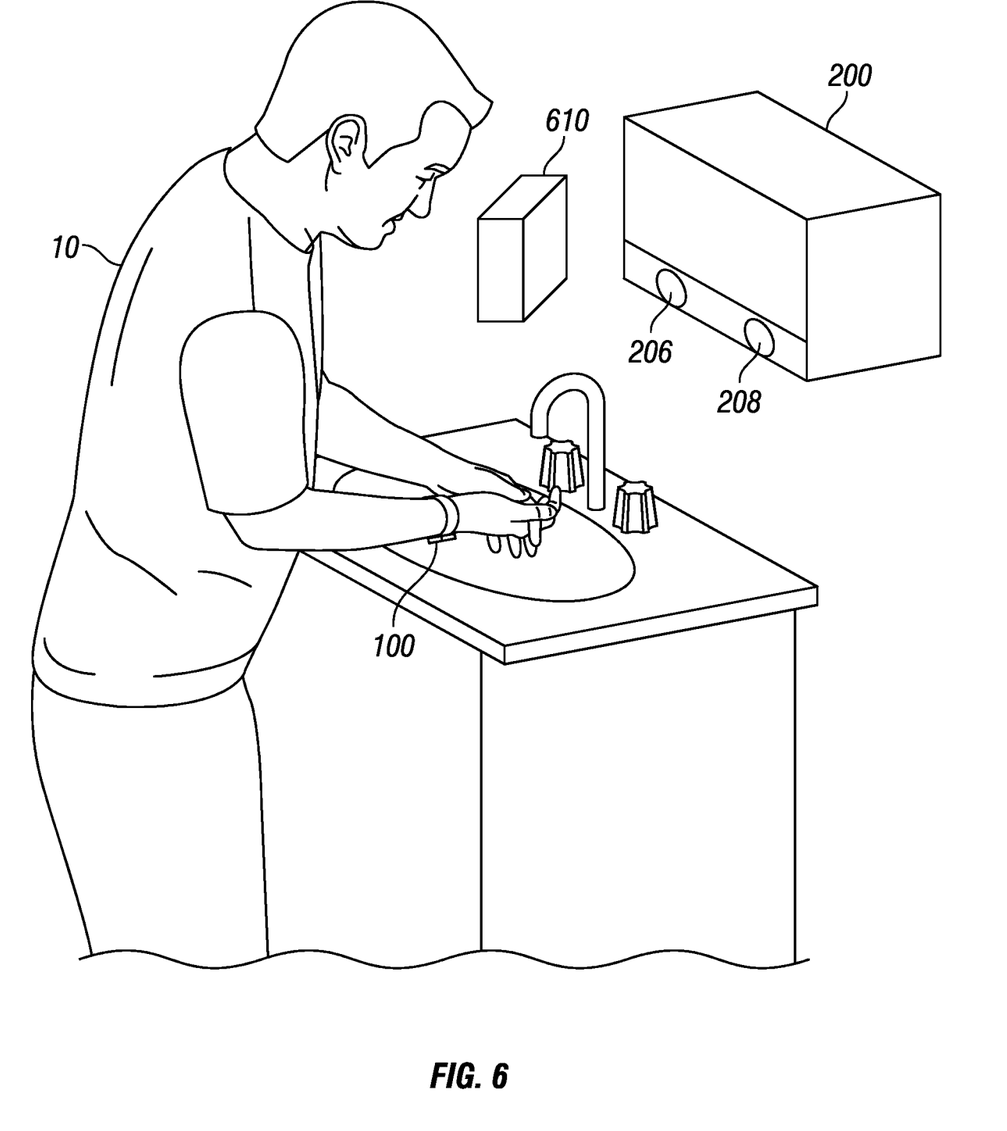
FIG. 6 is a perspective view of an embodiment of a user at a hygiene station.

Referring to FIG. 6, an embodiment of a user 10 washing their hands at a hygiene station with a wash node 200 is depicted. Upon receiving a notification by the wristband 100 to wash their hands, the user scans their wristband 100 with the wash node 200 to start the washing process. The wash node 200 may be placed at a location above the hygiene station that enables the camera 206 and/or sensor 208 to capture the act of the user washing their hands in the basin of the hygiene station. In some embodiments, the camera 206 may be located near the sink (from a distance of about 6 inches to about 2 feet) and angled to capture hand washing activity. Additionally, the wash node 200 may be positioned either to the left or the right of the hand washing sink, depending on the layout of the facility. Alternatively, the wash node 200 may be positioned above the hand washing sink. The wash node 200 may be configured to capture a series of images and/or video of the action in the basin of the hygiene station. The wash node 200 may be configured to communicate the images and/or video to the central controller for processing and storage. Once the user has successfully completed the washing sequence, as explained above, the wash node 200 communicates with the central controller to update the status of the user's wristband. In some embodiments, the wash node 200 may be configured to capture the user receiving a washing substance (e.g., soap) from a soap dispenser 610 that enable the central controller and/or database to detect the presence (if the washing substance and/or whether the user utilized a sufficient amount of washing substance during the hand washing activity.

In an alternative embodiment, the system may be adapted to monitor and maintain glove change compliance. A user reports to a hygiene station with a wash node to change their gloves according to the hygiene policy. Upon receiving a notification by the wristband to change their gloves, the user scans their wristband with the wash node to start the changing process. The wash node may be placed at a location above the hygiene station that enables the camera and/or sensor to capture the act of the user changing their gloves. In some embodiments, the camera 206 may be located near the changing area of the hygiene station (from a distance of about 6 inches to about 2 feet) and angled to capture glove changing activity. Additionally, the wash node may be positioned either to the left or the right of the hygiene station, depending on the layout of the facility. Alternatively, the wash node may be positioned above the hygiene station. The wash node may be configured to capture a series of images and/or video of the action in the changing area of the hygiene station. The wash node may be configured to communicate the images and/or video to the central controller for processing and storage. Once the user has successfully completed the changing sequence, as explained above, the wash node communicates with the central controller to update the status of the user's wristband.

In one configuration of glove changing compliance, the user may receive a default indication on the wristband that indicates the user is out of compliance with a glove changing policy, prompting the user to go to a glove station. The user will scan the wristband with the sensor, which changes the default indication to a cleaning indication. An example of a cleaning indication may be a flashing blue light. Upon receiving the cleaning indication, the timer begins to run for a first period of time (between about 10 second and about 20 seconds) that the user must change out their gloves for clean gloves. After the timer runs for the first period of time, the cleaning indication changes to a cleaned indication. An example of a cleaned indication may be a solid blue light.

Once the user receives the cleaned indication and changed out the gloves, the user scans the wristband, which changes the cleaned indication to a compliant indication. An example of a compliant indication may be a solid green light. After receiving the compliant indication, the controller runs the timer for a second period of time (from about 1 minute to about 30 minutes). After about 25 minutes have elapsed, the controller sends a warning signal to the wristband, which changes the cleaned indication to a warning indication. An example of a warning indication may be a yellow light. At this point, the user may proceed to the glove station to changeout their gloves or wait for the second period of time to run. Once the second period of time runs, the controller sends a default signal to the wristband, which changes the warning signal to a default signal. An example of a default signal may be a flashing red light. In some embodiments, the controller uploads all of the information captured by the sensor to the server.

In an alternative embodiment, the system may be adapted to monitor and maintain hand sanitizing compliance. A user reports to a hygiene station with a wash node to sanitize their hands according to the hygiene policy. Upon receiving a notification by the wristband to sanitize their hands, the user scans their wristband with the wash node to start the sanitizing process. The wash node may be placed at a location above the hygiene station that enables the camera and/or sensor to capture the act of the user sanitizing their hands. In some embodiments, the camera may be located near the sanitizing area of the hygiene station (from a distance of about 6 inches to about 2 feet) and angled to capture glove sanitizing activity. Additionally, the wash node may be positioned either to the left or the right of the hygiene station, depending on the layout of the facility. Alternatively, the wash node may be positioned above the hygiene station. The wash node may be configured to capture a series of images and/or video of the action in the sanitizing area of the hygiene station. The wash node may be configured to communicate the images and/or video to the central controller for processing and storage. Once the user has successfully completed the sanitizing sequence, as explained above, the wash node communicates with the central controller to update the status of the user's wristband.

In one configuration of hand sanitizing compliance, the user may receive a default indication on the wristband that indicates the user may be out of compliance with a hand sanitizing policy, prompting the user to go to a sanitizing station. The user will scan the wristband with the sensor, which changes the default indication to a cleaning indication. An example of a cleaning indication may be a flashing blue light. Upon receiving the cleaning indication, the timer begins to run for a first period of time (between about 10 second and about 20 seconds) that the user must sanitize their hands. After the timer runs for the first period of time, the cleaning indication changes to a cleaned indication. An example of a cleaned indication may be a solid blue light.

Once the user receives the cleaned indication the user scans the wristband, which changes the cleaned indication to a compliant indication. An example of a compliant indication may be a solid green light. After receiving the compliant indication, the controller runs the timer for a second period of time (from about 1 minute to about 30 minutes). After about 25 minutes have elapsed, the controller sends a warning signal to the wristband, which changes the cleaned indication to a warning indication. An example of a warning indication may be a yellow light. At this point, the user may proceed to the hygiene station to sanitize their hands or wait for the second period of time to run. Once the second period of time runs, the controller sends a default signal to the wristband, which changes the warning signal to a default signal. An example of a default signal may be a flashing red light. In some embodiments, the controller uploads all of the information captured by the sensor to the server.

While this disclosure has been particularly shown and described with reference to preferred embodiments, it will be understood by those skilled in the art that various changes in form and detail may be made therein without departing from the spirit and scope of the invention. The inventors expect skilled artisans to employ such variations as appropriate, and the inventors intend the invention to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

While various embodiments in accordance with the principles disclosed herein have been described above, it should be understood that they have been presented by way of example only, and not limitation. Thus, the breadth and scope of this disclosure should not be limited by any of the above-described exemplary embodiments but should be defined only in accordance with any claims and their equivalents issuing from this disclosure. Furthermore, the above advantages and features are provided in described embodiments but shall not limit the application of such issued claims to processes and structures accomplishing any or all of the above advantages.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically, and by way of example, although the headings refer to a "Technical Field," the claims should not be limited by the language chosen under this heading to describe the so-called field. Further, a description of a technology as background information is not to be construed as an admission that certain technology is prior art to any embodiment(s) in this disclosure. Neither is the "Brief Summary" to be considered as a characterization of the embodiment(s) set forth in issued claims. Furthermore, any reference in this disclosure to "invention" in the singular should not be used to argue that there is only a single point of novelty in this disclosure. Multiple embodiments may be set forth according to the limitations of the multiple claims issuing from this disclosure, and such claims accordingly define the embodiment(s), and their equivalents, that are protected thereby. In all instances, the scope of such claims shall be considered on their own merits in light of this disclosure but should not be constrained by the headings set forth herein.

What is claimed:

1. A method of maintaining compliance with a wash protocol, comprising:
  scanning a portable electronic device with a wash node to start a timer;
  receiving a first indication on the portable electronic device that the wash protocol has been initiated;
  obtaining wash data;

scanning the portable electronic device with the wash node to stop the timer;
receiving a second indication on the portable electronic device that the wash protocol has been terminated; and
determining compliance of the wash protocol based on an elapsed time between the start and the stop of the timer.

2. The method of claim 1, further comprising receiving a third indication on the portable electronic device that the compliance of the wash protocol has been satisfied when the elapsed time exceeds a threshold time value, wherein the first indication comprises a first color light, the second indication comprises a second color light, and the third indication comprises a third color light.

3. The method of claim 1, further comprising receiving a third indication on the portable electronic device that the wash protocol has not been satisfied when the elapsed time does not exceed a threshold time value thereby causing the wash protocol to be restarted, wherein the first indication comprises a first color light, the second indication comprises a second color light, and the third indication comprises a third color light.

4. The method of claim 1, wherein the step of determining compliance is further based on an analysis of the wash data obtained during the elapsed time.

5. The method of claim 2, further comprising:
in response to receiving the third indication, starting the timer for a first predetermined amount of time; and
receiving, after the first predetermined amount time expires, a fourth indication on the portable electronic device that compliance with the wash protocol is about to expire, wherein the fourth indication comprises a fourth color light.

6. The method of claim 5, further comprising:
in response to receiving the fourth indication, starting the timer for a second predetermined amount of time; and
receiving, after the second predetermined amount of time expires, a fifth indication on the portable electronic device that compliance with the wash protocol has expired, wherein the fifth indication comprises a fifth color light.

7. The method of claim 1, wherein the portable electronic device includes a heat sensor configured to capture a temperature of a user, a gyroscope configured to capture movement of a user, a positional sensor configured to capture positioning information of the user, and wherein the wash data includes body temperature, user movement, and positioning information.

8. The method of claim 7, further comprising analyzing detected hand washing movement and cross-referencing the detected hand washing movement with effective hand washing techniques to determine whether the compliance of the wash protocol has been satisfied.

9. The method of claim 5, further comprising:
recording the compliance of the wash protocol in a database for display on a compliance dashboard; and
recording the compliance with the wash protocol is about to expire in the database for display on the compliance dashboard.

10. The method of claim 6, further comprising recording the compliance with the wash protocol has expired in a database for display on a compliance dashboard.

11. A system for monitoring and maintaining compliance with a wash protocol, the system comprising:
a portable electronic device associated with a unique identifier;
a wash node communicatively coupled to the portable electronic device, the wash node having a set of sensors, wherein the wash node is configured to capture wash data with the set of sensors, wherein further the wash data comprises photographs, infrared images, or video; and
a processor communicatively coupled to the wash node and the portable electronic device, wherein the processor is configured to determine compliance with the wash protocol;
wherein the system is configured to:
start a timer based on a first scan between the portable electronic device and the wash node, wherein the portable electronic device receives a first indication that the wash protocol has been initiated;
associate the wash data captured by the wash node with the unique identifier;
stop the timer based on a second scan between the portable electronic device and the wash node, wherein the portable electronic device receives a second indication that the wash protocol has been terminated;
determine compliance of the wash protocol based on an elapsed time between the start and the stop of the timer;
transmit results of the determination to the portable electronic device; and
store the results of the determination in a database.

12. The system of claim 11, wherein the system is further configured to:
when the elapsed time exceeds a threshold time value, transmit a third indication to the portable electronic device indicating that the compliance of the wash protocol has been satisfied, wherein further the first indication comprises a first color light, the second indication comprises a second color light, and the third indication comprises a third color light.

13. The system of claim 12, wherein the system is further configured to:
after the third indication is transmitted to the portable electronic device, start the timer for a first predetermined amount of time, wherein a fourth indication is transmitted to the portable electronic device indicating that the compliance with the wash protocol is about to expire when the first predetermined amount of time expires, and wherein the fourth indication comprises a fourth color light.

14. The system of claim 13, wherein the system is further configured to:
after the fourth indication is transmitted to the portable electronic device, start the timer for a second predetermined amount of time, wherein a fifth indication is transmitted to the portable electronic device indicating that the compliance with the wash protocol has expired when the second predetermined amount of time expires, and wherein the fifth indication comprises a fifth color light.

15. The system of claim 11, wherein the portable electronic device includes a heat sensor configured to capture a temperature of a user, a gyroscope configured to capture movement of a user, a positional sensor configured to capture positioning information of the user, wherein further the wash data includes body temperature, user movement, and positioning information.

16. The system of claim 11, wherein the processor is communicatively coupled to the database that is configured to display wash protocol compliance of the portable electronic device in a dashboard.

17. The system of claim 16, further comprising a kiosk communicatively coupled to the processor, wherein the kiosk is configured to associate the unique identifier with a user upon checkout of the portable electronic device from the kiosk, wherein further the kiosk is configured to disassociate the unique identifier with the user upon check-in of the portable electronic device to the kiosk, wherein further the dashboard reflects an up-to-date status of the compliance of the user.

18. The system of claim 17, further comprising a charging and sanitizing station, wherein the charging and sanitizing station is configured to charge and sanitize the portable electronic device.

19. The system of claim 17, wherein the processor is configured to determine a shift compliance rating of the user that is based on the saved determination between checkout and check-in of the portable electronic device from the kiosk, wherein further the processor is configured to determine an overall compliance rating of the user that is based on every saved determination associated with the unique identifier.

20. The system of claim 15, wherein the processor is configured to determine compliance of the wash protocol by analyzing detected hand washing movement and cross-referencing the detected hand washing movement with effective hand washing techniques.

\* \* \* \* \*